(12) United States Patent
Benner

(10) Patent No.: US 11,667,943 B1
(45) Date of Patent: Jun. 6, 2023

(54) DIRECTED TRANSLITERATION OF NUCLEOTIDES IN DNA

(71) Applicant: Steven A Benner, Gainesville, FL (US)

(72) Inventor: Steven A Benner, Gainesville, FL (US)

( * ) Notice: Subject to any disclaimer, the term of this patent is extended or adjusted under 35 U.S.C. 154(b) by 60 days.

(21) Appl. No.: 17/156,465

(22) Filed: Jan. 22, 2021

Related U.S. Application Data

(63) Continuation-in-part of application No. 16/572,078, filed on Sep. 16, 2019, now abandoned, which is a continuation-in-part of application No. 15/997,325, filed on Jun. 4, 2018, now Pat. No. 10,415,088, which is a continuation-in-part of application No. 14/218,405, filed on Mar. 18, 2014, now Pat. No. 9,988,659, which is a continuation-in-part of application No. 12/653,613, filed on Dec. 16, 2009, now Pat. No. 9,334,534.

(60) Provisional application No. 61/802,913, filed on Mar. 18, 2013.

(51) Int. Cl.
*C12P 19/34* (2006.01)
(52) U.S. Cl.
CPC .................................. *C12P 19/34* (2013.01)
(58) Field of Classification Search
CPC ............................ C12P 19/34; C12Q 1/6869
See application file for complete search history.

*Primary Examiner* — Jezia Riley

(57) ABSTRACT

Disclosed are PCR processes that transliterate target duplex DNA molecules containing 8 different nucleotide building blocks strategically arranged to allow efficient conversion of information in that target into DNA built from just four different nucleotides.

1 Claim, 2 Drawing Sheets

Figure 1:
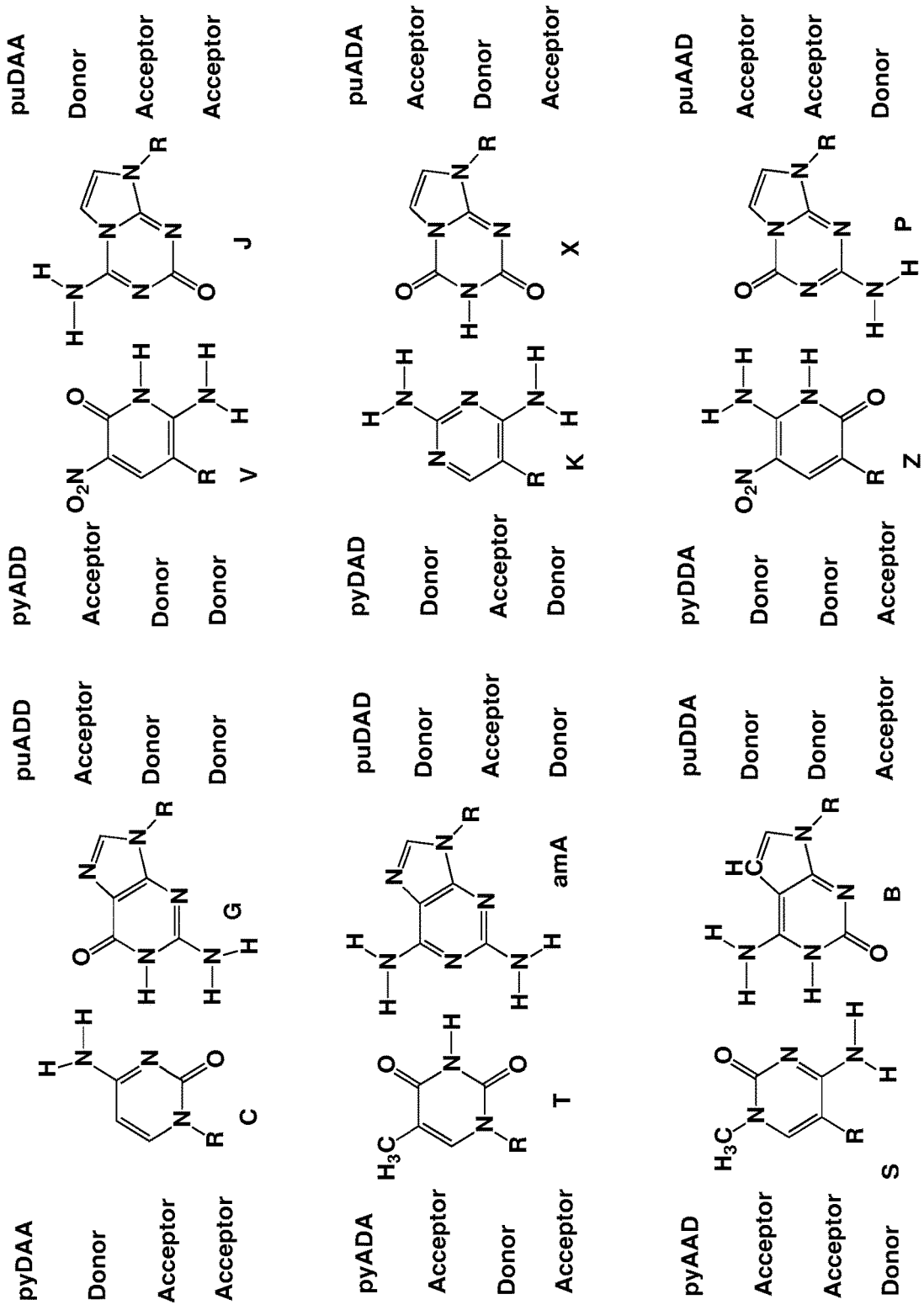

Specification includes a Sequence Listing.

DIRECTED TRANSLITERATION OF NUCLEOTIDES IN DNA

CROSS REFERENCE TO RELATED APPLICATIONS

This Application is a continuation in part of U.S. patent application Ser. No. 16/572,078, filed 16 Sep. 2019, currently pending, and entitled "Directed transliteration of nucleotides in DNA". U.S. patent application Ser. No. 16/572,078 is a continuation-in-part of U.S. patent application Ser. No. 15/997,325, filed Jun. 4, 2018, entitled "In Vivo Conversion of Nucleosides in Plasmid DNA", now issued as U.S. patent Ser. No. 10/415,088. U.S. patent application Ser. No. 15/997,325 is a continuation-in-part of U.S. patent application Ser. No. 14/218,405, filed Mar. 18, 2014, entitled "In Vivo Conversion of Nucleosides in Plasmid DNA", now issued as U.S. Pat. No. 9,988,659. U.S. patent application Ser. No. 14/218,405 is a continuation-in-part of U.S. patent application Ser. No. 12/653,613, filed Dec. 16, 2009, entitled "Processes replacing standard nucleotides by non-standard nucleotides and non-standard nucleotides by standard nucleotides in DNA", now issued as U.S. Pat. No. 9,334,534. U.S. patent application Ser. No. 14/218,405 also claims priority to U.S. provisional patent application 61/802,913, entitled "In vivo Conversion of Nucleosides in Plasmid DNA", which was filed Mar. 18, 2013.

STATEMENT OF RIGHTS TO INVENTIONS MADE UNDER FEDERALLY-SPONSORED RESEARCH

None.

The Names of the Parties to a Joint Research Agreement

Not applicable

Incorporation-By-Reference of Material Submitted on a Compact Disc

None

BACKGROUND OF THE INVENTION

(1) Field of the Invention

The field of this invention is nucleic acids and their analogs, more specifically nucleotide analogs that can form non-standard Watson-Crick nucleobase pairs that have geometry similar to the geometry of standard Watson-Crick pairs, but are joined by a non-standard hydrogen bonding patterns. More specifically, this invention relates to processes that use these in a process whereby they transiently serve to assemble fragments, and then are replaced by a transliteration process that mismatches standard nucleoside triphosphates against non-standard nucleotides in a template.

(2) Description of Related Art

Natural oligonucleotides bind to complementary oligonucleotides according to Watson and Crick rules of nucleobase pairing, where adenine (A) (or 2-aminoadenine) pairs with thymine (T) (or uracil, U), and guanine (G) pairs with cytosine (C), with complementary strands anti-parallel to one another. In this disclosure, "DNA" or "nucleic acid" is understood to include, as appropriate, both DNA (where the sugar is 2'-deoxyribose) and RNA (where the sugar is ribose), the 2'-O-alkyl and allyl derivatives. Further, these nucleic acids and their analogs may carrying tags (e.g., fluorescent, functionalized, or binding) to the ends, sugars, or nucleobases, and/or non-nucleotidic material attached to the ends of the strand.

These pairing rules, which can be applied without undue experimentation, allow specific hybridization of an oligonucleotide to a complementary oligonucleotide, making oligonucleotides valuable as probes in the laboratory, in diagnostics, as messages that can direct the synthesis of specific proteins, and in other applications well known in the art.

Further, pairing is used by enzymes to catalyze the synthesis of new oligonucleotide strands that are substantially complementary (>95% canonically paired) to template nucleotides. In this synthesis, building blocks (normally the triphosphates of ribo- or deoxyribonucleosides carrying of A, T, U, C, or G) are directed by a template oligonucleotide to form a complementary oligonucleotide with the complementary sequence. This serves as the basis for technologies for enzymatic synthesis and amplification of specific nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

The Watson-Crick pairing rules can be understood chemically as a consequence of two complementarity principles. The first is "size complementarity". In the standard Watson-Crick geometry, a large purine nucleobase pairs with a small pyrimidine nucleobase. This allows the AT pair to be nearly the same size as a GC nucleobase pair; the rungs of the DNA ladder, formed from AT and GC pairs, all have the same length. In this disclosure, to be "complementary in the Watson-Crick sense" means to have the Watson-Crick geometry, a full pairing (not wobble pairing) of a large purine and a small pyrimidine held together by three hydrogen bonds, or (if context demands) two hydrogen bonds, where in pairing is said to be "against" the nucleotide in the complementary strand, in an antiparallel orientation, to which it is matched.

The specificity of recognition between large and small nucleobases is determined by hydrogen bonding between the nucleobases. In standard nucleobases, hydrogen bond donors are heteroatoms (nitrogen or oxygen in the natural nucleobases) bearing a hydrogen, while hydrogen bond acceptors are heteroatoms (nitrogen or oxygen in the natural nucleobases) with a lone pair of electrons. In the Watson-Crick nucleobase pairing geometry, a six membered ring (in standard nucleobases, a pyrimidine) pairs with a ring system composed of a fused five-six ring system (in standard nucleobases, a purine), with a middle hydrogen bond linking two ring atoms, and hydrogen bonds on either side joining functional groups appended to each of the rings, with donor groups paired with acceptor groups. The AT nucleobase pair uses this hydrogen bonding pattern only partly; it is completely used in the diamino A:T base pair.

To systematize the nomenclature for the hydrogen bonding patterns, the hydrogen bonding pattern implemented on a small component of a nucleobase pair are designated by the prefix "py". Following this prefix is the order, from the major groove to the minor groove, of hydrogen bond acceptor (A) and donor (D) groups. Thus, both thymine and uracil implement the standard hydrogen bonding pattern pyADA.

The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major to the minor grooves, using "A" and "D". Thus, the standard nucleobases adenine and guanine implement the standard hydrogen bonding patterns puDA- and puADD respectively.

A teaching of this disclosure is that hydrogen-bonding patterns designated using this systematic nomenclature are distinct in concept from the organic molecules that are used to implement the hydrogen-bonding patterns. Thus, guanosine is a nucleoside that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen-bonding pattern determines, in large part, the utility of the non-standard hydrogen-bonding pattern, in various applications to which it might be applied.

Here, 2-amino-5-methyl-1-(1'-beta-D-2'-deoxyribofuranosyl)-4(1H)-pyrimidine, also known as 2'-deoxyisocytidine, disoC, and isoC, all implement the pyAAD hydrogen bonding pattern, designated here as S. Implementing its complementary puDDA hydrogen bonding pattern B is, for example, 6-amino-1, 9-dihydro-9- (1'-beta-D-T-deoxyribofuranosyl)-3H-purin-2-one, also known as 2'-deoxyisoguanosine, disoG, or isoG, as does the 7-deaza-isoG analog.

One advantage of incorporating non-standard nucleotides into human diagnostic assays is that binding between oligonucleotides containing these can occur without interference from natural DNA, which is often present in abundance in samples taken from human tissues. Further, adding information density in an 8 letter alphabet provides more control over the assembly of many fragments to give double helix structures.

However, oligonucleotides containing non-standard nucleotides, including 8-letter GACTZPSB DNA, cannot today be introduced into standard cloning systems. No strain used for cloning, including E. coli strains, is known to have the cellular machinery for making the triphosphates of non-standard nucleosides and using them to replicate DNA containing non-standard nucleotides.

Therefore, a process that accepts duplexes built from 8 nucleotides and, during PCR converts them into entirely standard DNA double helices without losing information would have utility.

Mismatching is known between non-standard and standard pairs such that a standard nucleotide is incorporated opposite a nonstandard nucleotide in the template. For example, Sepiol et al. [Sepiol et al. 1976] recognized that isoG, which presents a hydrogen bond donor-donor-acceptor pattern complementary to the acceptor-acceptor-donor pattern of isoC, exists in water to about 10% as an enol tautomeric form, which can present a hydrogen bond donor-acceptor-donor hydrogen bonding pattern complementary to T (acceptor-donor-acceptor). Work in the 1990's showed that polymerases of various types would incorporate T (or U) opposite isoG in a template, presumably by pairing between T (or U) and the minor tautomeric form of isoG [Switzer et al. 1993]. This caused the loss of the isoG:isoC pair in (for example) PCR reactions[Johnson et al. 2004], a loss that was considered throughout the art to be disadvantageous, as it appeared to deprive the product from the possibility of the PCR product of having the orthogonal isoC:isoG pair.

To suppress this mispairing between T and the minor tautomeric form of isoG, T was replaced with 2-thioT in a polymerase incubation [Sismour et al. 2005]. Here, products derived from a six letter PCR incorporating A, G, C, 2-thioT, isoG and isoC was able to retain the isoC and isoG non-standard components after many more cycles than a six letter PCR where standard T was used instead of 2-thioT. Thus, the products were able to retain the ability to be orthogonally bound by isoG:isoC pairing after many more cycles of PCR. Further attempting to avoid mispairing and isoG:T (or U) mismatching, 7-deazaisoG was developed [Martinot et al. 2004].

These examples from the prior art show the extent to which those in the art view as undesirable the mismatching between standard nucleotides and non-standard nucleotides, and thereby teach away from the instant invention, which is based on an inventive step that recognizes the utility of mismatching.

BRIEF SUMMARY OF THE INVENTION

In contrast with the art cited above, the purpose of the instant invention is to mismatch nonstandard nucleotides that contains as eight different nucleotides (GACTZPSB) in a duplex cleanly, to allow the production of a fully standard oligonucleotide duplex by PCR while substantially retaining (>98%) the information that is encoded in the initial duplex. This requires strategic separation of standard and nonstandard nucleotides in the two strands. In particular, one strand should contain G, A, C, T, Z and B, but no S or P, and the other strand should contain G, A, C, T, P and S, but no Z or B.

BRIEF DESCRIPTION OF THE SEVERAL VIEWS OF THE DRAWING(S)

FIG. 1. One set of nucleosides implementing the hydrogen bonding patterns of 1 12 "letter" "artificially expanded genetic information system" (AEGIS). Nucleobase pairs have Watson-Crick geometries, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. The heterocycles shown are the currently preferred implementations of the indicated hydrogen bonding patterns; others are conceivable. Electron density presented to the minor groove is shown by the shaded lobes. Note that some non-standard pyrimidines do not present this density. The nucleotides implementing the pyDDA:puAAD hydrogen bonding pattern, the topic of this paper, are at the bottom right.

Figure 2:
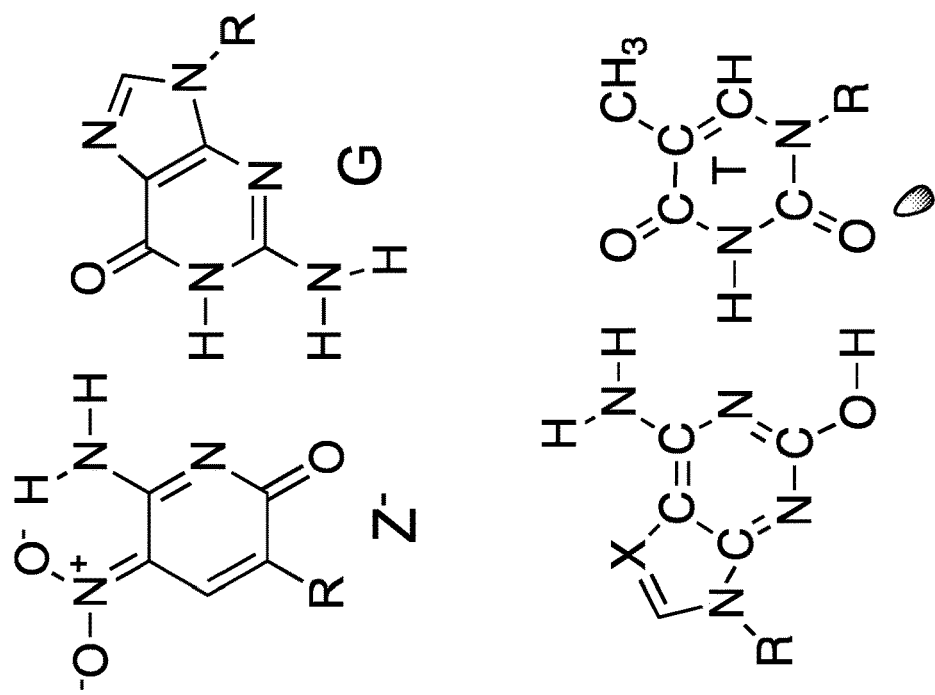
Figure 2:
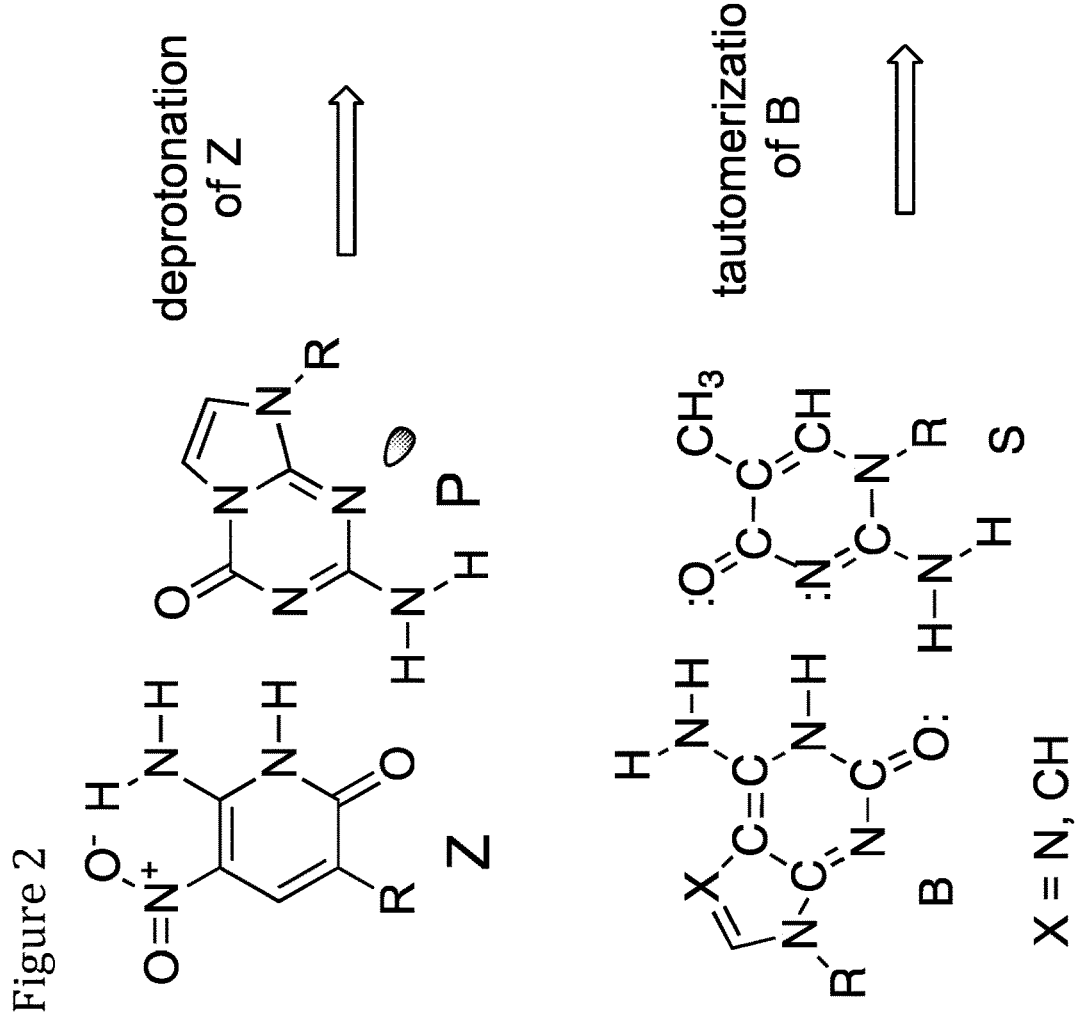

FIG. 2. (top) Mismatches that allow transliteration during PCR of a duplex that has Z:P pairs; these correspond to C:G pairs in the amplicon duplex. (bottom) Mismatches that allow transliteration during PCR of a duplex that has S:B pairs; these correspond to T:A pairs in the amplicon duplex.

DETAILED DESCRIPTION OF THE INVENTION

The first inventive step in creating these processes was to set aside the prohibition in the art against mismatching, to recognize that mismatches introduced by polymerase copying might be useful.

The next inventive step recognized that polymerases may be involved in processes that end up creating replicates or complements where standard components are replaced by non-standard components with sequence specificity, or where non-standard components are replaced by standard components (the vice versa process is also achievable in this way, and in the ways described below). It was recognized that this could be done in two ways. In the first, the non-standard nucleotide is directly incorporated opposite a standard nucleotide. In the second, an intermediary nucleotide, having a structure that is neither standard or, in the sense used here, non-standard, might be incorporated opposite the standard nucleotide to give an intermediary oligonucleotide product, and the intermediary oligonucleotide product can be copied using a polymerase and the appropriate triphosphates to give a final product that contains the canonical non-standard nucleotide(s).

Several ways to achieve such replacement were then recognized as further inventive steps. Consider first the direct incorporation of a non-standard nucleotide opposite a standard nucleotide. The nucleobases can be either bases or acids, and therefore adopt protonated and deprotonated forms, respectively. In these protonated and deprotonated forms, the hydrogen bonding pattern that is presented to the complementary nucleobases is different from in the normal form. For example (FIG. 2), while the pyDDA nucleobase implemented as 6-amino-3-(2'-deoxy)-D-ribofuranosyl)-5-nitro-1H-pyridin-2-one (dZ) is complementary to the puAAD nucleobase implemented as 2-amino-1,9-dihydro-5-aza-3,7-dideaza-9- (1'-beta-D-2'-deoxyribofuranosyl)-1H-purin-6-one, also known as 7-amino-9-(1'-beta-D-T-deoxyribofuranosyl)-imidazo[1,2-c]pyrimidin-5(1H)-one (dP), its deprotonated form is complementary to G (puADD).

Conditions can be adjusted to facilitate this. While not wishing to be bound by theory, mismatches between dP and standard nucleotides and mismatches between dZ and standard nucleotides do not arise from minor tautomeric forms of non-standard and standard nucleobases, but rather by their protonation and deprotonation.

Likewise, deprotonation of the pyDDA heterocycle generates a species that is complementary to G. Conversely, deprotonation of dG generates a species that is Watson-Crick complementary to dZ. Under this mechanism, high pH favors the dZ mismatch. Experimental studies showed that this was the case; dP is incorporated opposite dC at lower pH (FIG. 3).

Experimental work showed that if the pH is adjusted accordingly, and if a primer extension reaction is performed without dCTP or dGTP respectively, dZ is incorporated opposite template dG at high pHs. In the example above, the sequence 5'-ATGCTTAC-3' generates a copy having the sequence 5'-GTAAGZAT-3' and 5'-PTAAPCT-3'. A screen of polymerases identified several that would do this efficiently, including incorporating non-standard components consecutively opposite the same standard component presented consecutively in the template.

This can also be done by direct replacement during PCR if the non-standard nucleobase has a minor tautomeric form that is complementary to the standard nucleobase. This can be done through incubations that lacked the standard nucleoside triphosphate complement, or by doing template-directed primer extension under conditions adjusted so as to favor the mismatch. For example, if an analyte is used as a template in a primed polymerase reaction where isoG is presented as a triphosphate without dATP, an oligonucleotide with a defined sequence (for illustration, let us choose an arbitrary sequence that is shorter than one that would be useful, but is sufficiently short as to not require a sequence listing, 5'-ATGCTTAC-3'), one would generate the product 5'-GT(isoG)(isoG)GC(isoG)T-3'. This would be captured on a probe containing the non-standard sequence 5'-A(isoC)GC(isoC)(isoC)AC-3'. Thus, the analyte would lead to a specific orthogonal sequence without the need for a tag.

The predecessor patents have shown that transliteration can go in both directions and, depending on pH, can involve multiple nucleotides. Thus, to replace the Z:P pair in the starting duplex it is to be PCR amplified, transliteration can rely on protonated C mismatching with P, or deprotonated Z mismatching with G.

However, that are neglected to understand that different kinds of mismatches have different efficiencies, retain information differentially, and therefore have different utilities.

The elements of discovery that gave rise to the instant invention arose from the observation that the mismatching of GTP opposite template Z is far more efficient, and gave more reliable transliteration without loss of information under standard PCR conditions, than the mismatching of CTP opposite template P. Further, a second set of observations discovered that the mismatching of standard T opposite template B was far more efficient, and gave more reliable transliteration without loss of information under standard PCR conditions, than mismatching of any natural nucleoside triphosphate opposite template S.

Accordingly, the instant invention teaches that PCR amplification of DNA duplexes composed of the eight nucleotides, four standard (G, A, C, and T, which need not be all president any single-strand) and the four nonstandard (S, B, Z, P) is advantageously performed when the eight different nucleotides are not evenly distributed in the two strands. Rather, this invention teaches that one strand should contain all the Z and B components, as well as the standard for nucleotides G, A, C, and T. Its complementary strand therefore must contain all of the P and S components, as well as the standard four nucleotides G, A, C, and T.

The presently preferred implementation of the instant invention does PCR with both the forward and reverse primers present, but with the triphosphates of G, A, C, and T, as well as dZTP and dBTP.

As illustrated in the examples of the parent patent application, the PCR is run under normal conditions, as well known in the art, with temperature cycling, in buffered aqueous media, with polymerases such as the DNA polymerase from *Thermus aquaticus*.

LITERATURE

Brownie, J., Shawcross, S., Theaker, J., Whitcombe, D., Ferrie, R., Newton, C., Little, S. (1997). The elimination of primer-dimer accumulation in PCR. *Nucleic Acids Res.* 25, 3235-3241

Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.*, 42, 3120-3127.

Elbeik, T., Surtihadi, J., Destree, M., Gorlin, J., Holodniy, M., Jortani, S. A., Kuramoto, K., Ng, V., Valdes, R., Valsamakis, A. et al. (2004) Multicenter evaluation of the performance characteristics of the Bayer VERSANT HCV RNA 3.0 assay (bDNA). *J. Clin. Microbiol.*, 42, 563-569.

Horlacher, J., Hottiger, M., Podust, V. N., Hübscher, U., Benner, S. A. (1995) Recognition by viral and cellular DNA polymerases of nucleosides bearing bases with non-standard hydrogen bonding patterns. *Proc. Natl. Acad. Sci.*, 92, 6329-6333

Hutter, D. and Benner, S. A. (2003) Expanding the genetic alphabet. Non-epimerizing nucleoside with the pyDDA hydrogen bonding pattern. *J. Org. Chem.*, 68, 9839-9842

Johnson, S. C., Sherrill, C. B., Marshall, D. J., Moser, M. J., Prudent, J. R. (2004) A third base pair for the polymerase chain reaction: inserting isoC and isoG. *Nucleic Acids Res.* 32, 1937-1941

Jurczyk, S. C., Horlacher, J., Devine, K. G., Benner, S. A., Battersby, T. R. (2000) Synthesis and characterization of oligonucleotides containing 2'-deoxyxanthosine using phosphoramidite chemistry. *Helv. Chim. Acta* 83, 1517-1524

Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphoramidite chemistry. *Helv. Chim. Acta* 81, 793-811]

Jurczyk, S. C., Battersby, T. R., Kodra, J. T., Park, J.-H., Benner, S. A. (1999) Synthesis of 2'-deoxyisoguanosine triphosphate and 2'-deoxy-5-methyl-isocytidine triphosphate. *Helv. Chim. Acta.* 82, 1005-1015

Kim, H. J., Leal, N. A., Benner, S. A. (2009) 2'-Deoxy-1-methylpseudocytidine, a stable analog of 2'-deoxy-5-methylisocytidine. *Bioorg Med. Chem.* 17, 3728-373

Kodra, J., Benner, S. A. (1997) Synthesis of an N-alkyl derivative of 2'-deoxyisoguanosine. *Syn. Lett.*, 939-940

Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798]

Martinot, T. A., Benner, S. A. (2004) Expanding the genetic alphabet: 7-Deaza-isoguanosine favors the 1N—H keto form by $10^3$-to-1 over the enol. *J. Org. Chem.* 69, 3972-3975

Murakami, K., Shirasaka, T., Yoshioka, H., Kojima, E., Aoki, S., Ford, Jr., H., Driscoll, J. S., Kelley, J. A., Mitsuya, H. (1991) *Escherichia coli* mediated biosynthesis and in vitro Anti-HIV Activity of lipophilic 6-Halo-2',3'-dideoxypurine nucleosides. *J. Med. Chem.* 34, 1606-1612

Piccirilli, J. A., Krauch, T., Moroney, S. E., Benner, S. A. (1990) Extending the genetic alphabet. Enzymatic incorporation of a new base pair into DNA and RNA. *Nature* 343, 33-37

Piccirilli, J. A., Krauch, T., MacPherson, L. J., Benner, S. A. (1991) A direct route to 3-(ribofuranosyl)-pyridine nucleosides. *Helv. Chim. Acta* 74, 397-406

Sepiol, J., Kazimierczuk, Z., Shugar, D. Z. (1976) Tautomerism of iso-guanosine and solvent-induced keto-enol equilibrium. *Z. Naturforsch* 31C, 361-370

Sismour, A. M., Benner, S. A. (2005) The use of thymidine analogs to improve the replication of an extra DNA base pair: A synthetic biological system. *Nucl. Acids Res.* 33, 5640-5646

Switzer, C. Y., Moroney, S. E., Benner, S. A. (1989) Enzymatic incorporation of a new base pair into DNA and RNA. *J. Am. Chem. Soc.* 111, 8322-8323

Switzer, C. Y., Moroney, S. E., Benner, S. A. (1993) Enzymatic recognition of the base pair between iso-cytidine and iso-guanosine. *Biochemistry* 32, 10489-10496

Tang, Y., Ramaiah, M., Vince, R. (2006) Synthesis and biological evaluation of carboacyclic nucleosides with (Z) and (E)-9-[4,4-bis(hydroxymethyl)]-2-butenyl side chain. *Bioorg. Med. Chem. Lett.* 14, 5866-5875

Voegel, J. J., von Krosigk, U., Benner, S. A. (1993) Synthesis and tautomeric equilibrium of 6-amino-5-benzyl-3-methylpyrazin-2-one. An acceptor-donor-donor nucleoside base analog. *J. Org. Chem.* 58, 7542-7547

Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880

Voegel, J. J., Benner, S. A. (1996) Synthesis, molecular recognition & enzymology of oligonucleotides containing the non-standard base pair between 5-aza-7-deaza-iso-guanine & 6-amino-3-methylpyrazin-2-one, a donor-acceptor-acceptor purine analog and an acceptor-donor-donor pyrimidine analog. *Helv. Chim. Acta* 79, 1881-1898 von Krosigk, U., Benner, S. A. (1995) pH-independent triple helix formation by an oligonucleotide containing a pyrazine donor-donor-acceptor base. *J. Am. Chem. Soc.* 117, 5361-5362

Yang, Z., Hutter, D., Sheng, P., Sismour, A. M. and Benner, S. A. (2006) Artificially expanded genetic information system. A new base pair with an alternative hydrogen bonding Yang, Z., Sismour, A. M., Sheng, P., Puskar, N. L., Benner, S. A. (2007) Enzymatic incorporation of a third nucleobase pair. *Nucl. Acids Res.* 35, 4238-4249

EXAMPLE

Example 1. Incorporating dZ into Oligonucleotides Opposite dG Via Primer Extension Using Therminator™ DNA Polymerase Summary of the results: The dZ containing oligo can be efficiently generated through primer extension using standard template and THERMINATOR™ DNA polymerase. These data are shown in FIG. 7 and FIG. 8.

Oligonucleotides Used in this Example:

Oligonucleotides for glyceraldehyde-3-phosphate dehydrogenase (GAP) Lua3-Std24-Biot:

```
                                       SEQ. ID. NO. 1
3'-CTA ACA TTC TAA ACT ATT TCA CAT-Biot-5'

SEQ. ID. NO. 2
3'-CTA ACA TTC TAA ACT ATT TCA CAT-
GGACTGGACGGCAGATCTTTT-Biot-5'

GAP-prim-21-Biot:
                                       SEQ. ID. NO. 3
3'-ZTA AZA TTZ TAA AZT ATT TZA ZAT-
GGACTGGACGGCAGATCTTTT-Biot-5'

GAP-F-Std45:
                                       SEQ. ID. NO. 4
5'-GAT TGT AAG ATT TGA TAA AGT GTA
CCTGACCTGCCGTCTAGAAAA-3'

GAP-prim-21-Biot:
                                       SEQ. ID. NO. 5
3'-CTA AZA TTZ TAA AZT ATT TZA ZAT-
GGACTGGACGGCAGATCTTTT-Biot-5'

GAP-F-45-5P:
                                       SEQ. ID. NO. 6
5'-GAT TPT AAP ATT TPA TAA APT PTA
CCTGACCTGCCGTCTAGAAAA-3'
```

Oligonucleotides for Topoisomerase (TOP)

Lua10-Std24-Biot:
SEQ. ID. NO. 7
3'-ACA TCT AAA CAT ACA TAC ATA CTA-Biot-5'

SEQ. ID. NO. 8
3'-ACA TCT AAA CAT ACA TAC ATA CTA-
CTGTCGGGGCCTACTCTTG-Biot-5'

TOP-prim-19-Biot:
SEQ. ID. NO. 9
3'-AZA TZT AAA ZAT AZA TAZ ATA ZTA-
CTGTCGGGGCCTACTCTTG-Biot-5'

Top-F-Std43:
SEQ. ID. NO. 10
5'-TGT AGA TTT GTA TGT ATG TAT GAT
GACAGCCCCGGATGAGAAC-3'

TOP-prim-19-Biot:
SEQ. ID. NO. 11
3'-ACA TZT AAA ZAT AZA TAZ ATA ZTA-
CTGTCGGGGCCTACTCTTG-Biot-5'

Top-F-43-5P:
SEQ. ID. NO. 12
5'-TGT APA TTT PTA TPT ATP TAT PAT
GACAGCCCCGGATGAGAAC-3'

Oligonucleotides for human epidermal growth factor
(HBE)
Lua14-Std24-Biot:
SEQ. ID. NO. 13
3'-TTT CAT ATC ATT CTA CAT ATC ATC-Biot-5'

SEQ. ID. NO. 14
3'-TTT CAT ATC ATT CTA CAT ATC ATC-
CGGGGTCAACGGCAGATCCT-Biot-5'

HBE-prim-20-Biot:
SEQ. ID. NO. 15
3'-TTT ZAT ATZ ATT ZTA ZAT ATZ AT-
CGGGGTCAACGGCAGATCCT-Biot-5'

HBE-F-Std43:
SEQ. ID. NO. 16
5'-AAA GTA TAG TAA GAT GTA TAG TA
GCCCCAGTTGCCGTCTAGGA-3'

HBE-prim-20-Biot:
SEQ. ID. NO. 15
3'-TTT ZAT ATZ ATT ZTA ZAT ATZ AT-
CGGGGTCAACGGCAGATCCT-Biot-5'

HBE-F-43-5P:
SEQ. ID. NO. 17
5'-AAA PTA TAP TAA PAT PTA TAP TA
GCCCCAGTTGCCGTCTAGGA-3'

Oligonucleotides for the Myc gene (MYC)
Lua19-Std24-Biot:
SEQ. ID. NO. 18
3'-CAT AAA CTC ATT CAT TAA CTA ACT-Biot-5'

SEQ. ID. NO. 19
3'-CAT AAA CTC ATT CAT TAA CTA ACT-
AGGAGGAATACGGAGATAGTA-Biot-5'

MYC-prim-21-Biot:
SEQ. ID. NO. 20
3'-ZAT AAA ZTZ ATT ZAT TAA ZTA AZT-
AGGAGGAATACGGAGATAGTA-Biot-5'

MYC-F-Std45:
SEQ. ID. NO. 21
5'-GTA TTT GAG TAA GTA ATT GAT TGA
TCCTCCTTATGCCTCTATCAT-3'

MYC-prim-21-Biot:
SEQ. ID. NO. 22
3'-CAT AAA ZTZ ATT ZAT TAA ZTA AZT-
AGGAGGAATACGGAGATAGTA-Biot-5'

MYC-F-45-5P:
SEQ. ID. NO. 23
5'-GTA TTT PAP TAA PTA ATT PAT TPA
TCCTCCTTATGCCTCTATCAT-3'

Protocol for the Primer Extension:

|  | 1 | 2 | 3 | 4 | 5 |
|---|---|---|---|---|---|
| γ-$^{32}$P-Primer (1 μM) | 0.1 μL | 0.1 μL | 0.1 μL | 0.1 μL | 0.1 μL |
| Biotin-Primer (1 uM) | 2 μL | 2 μL | 2 μL | 2 μL | 2 μL |
| Template (2 μM) | 1.5 μL Std-Temp | 1.5 μL Std-Temp | 1.5 μL Std-Temp | 1.5 μL dP Temp | 1.5 μL dP-Temp |
| 10x Thermopol Buffer (pH 9.0) | 1 μL | 1 μL | 1 μL | 1 μL | 1 μL |
| dNTP (1 mM) | 1 μL dA, T, G/TP | 1 μL dNTP | 1 μL dA, T, G, Z/TP | 1 μL dNTP | 1 μL dNTP + dZTP |
| DNA polymerase (1 U/μL) | 1 μL Therminator | 1 μL Therminator | 1 μL Therminator | 1 μL Taq | 1 μL Taq |
| H$_2$O (final volume of 10 μl) | 3.5 μL | 3.5 μL | 3.5 μL | 3.5 μL | 3.5 μL |

Note:

1 (negative control): Therminator, dATP + dTTP + dGTP;

2 (positive control): Therminator, dATP + dTTP + dGTP + dCTP;

3 (experiment): Therminator, dATP + dTTP + dGTP + dZTP;

4 (negative control): Taq, dNTP;

5 (experiment): Taq, dNTP + dZTP.

Primer Extension with $^{32}$P-Labeled Primer:

5'-$^{32}$P-Labeled primer (0.1 pmole plus cold primer (biotin-primer) 2 pmole, final assay concentration 210 nM) was annealed to either standard template or dP containing template (3 pmole, final assay concentration 300 nM) in thermpol reaction buffer by heating (5 min 95° C.) and then slow cooling (0.5 h) to room temperature. dNTP and DNA polymerase were added at room temperature, followed by incubating at 72° C. for 1 min or 5 min, and then, quenched by dilution into PAGE loading/quench buffer (8 μL, 10 mM EDTA in formamide). Samples were resolved by electrophoresis using a 16% PAGE (7 M urea). The gel was analyzed using MolecularImager software.

Primer Extension without $^{32}$P Labeled Primer:

Biotin-labeled primer (2 pmole, final assay concentration 200 nM) was annealed to either standard template or dP containing template (3 pmole, final assay concentration 300 nM) in thermpol reaction buffer by heating (5 min 95° C.) and then slow cooling (0.5 h) to room temperature. The biotin-labeled primer was extended under three different conditions: 2 (positive control): Therminator, dNTP; 3 (experiment): Therminator, dATP+dTTP+dGTP+dZTP; 5 (experiment): Taq, dNTP+dZTP. dNTP and DNA polymerase were added at room temperature, followed by incubating at 72° C. for 5 min. The reaction was quenched with 2 μL of 20 mM EDTA, and diluted with 190 μL of ddH$_2$O to give the fully extended full-length dZ containing or control oligonucleotide (final concentration 10 fmoles/μL).

1 (negative control): Therminator, dATP+dTTP+dGTP; 2 (positive control): Therminator, dATP+dTTP+dGTP+dCTP; 3 (experiment): Therminator, dATP+dTTP+dGTP+dZTP; 4 (negative control): Taq, dNTP; 5 (experiment): Taq, dNTP+dZTP.

What is claimed is:

1. A process for creating a preselected duplex DNA amplicon containing only standard 2'-deoxyribonucleotides, which have as their only nucleobases guanine, adenine, thymine, and cytosine, starting from a duplex target that contains those standard 2'-deoxyribonucleotides as well as four non-standard 2'-deoxyribonucleotides having the nucleobases

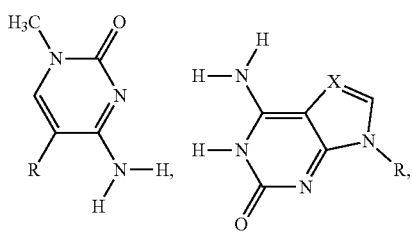

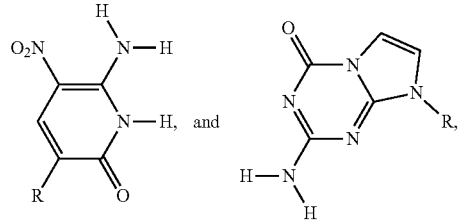

wherein R is the point of attachment of the nucleobase to a deoxyribose ring, said process comprising:

(a) mixing said duplex DNA target with preselected forward and reverse primers to form a resulting mixture, (b) incubating the resulting mixture with a polymerase in the presence of triphosphates of the four standard nucleosides, as well as the triphosphates of the two non-standard nucleosides having as their heterocyclic nucleobases

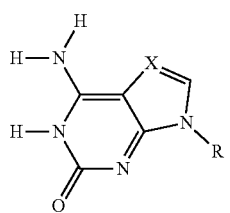 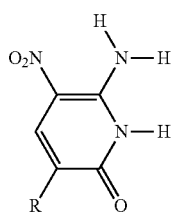
(c) performing a PCR reaction, wherein
(d) one strand of said target contains both
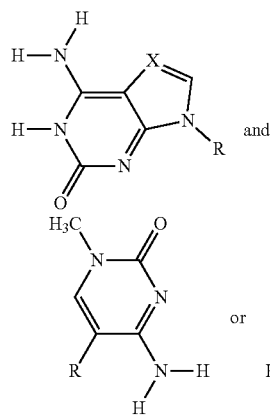 and 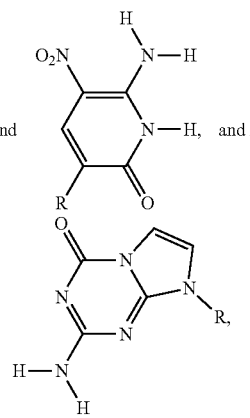, and no
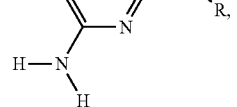
and the other strand of said target contains both
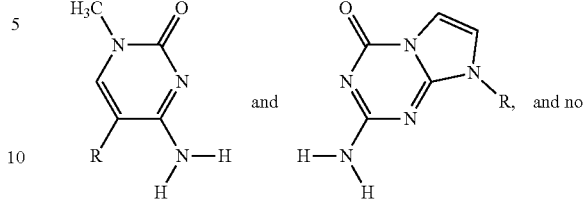 and 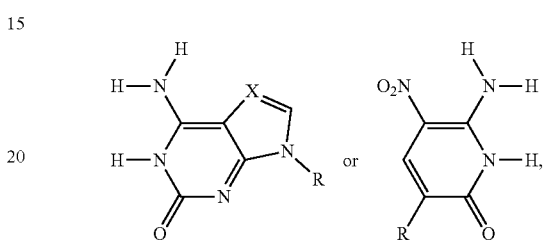, and no
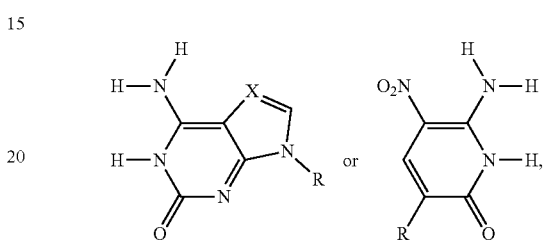 or 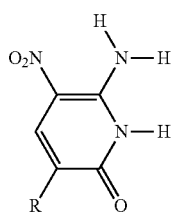,
and wherein
(e) X is either N or CH.
* * * * *

SEQUENCE LISTING

```
<160> NUMBER OF SEQ ID NOS: 23

<210> SEQ ID NO 1
<211> LENGTH: 24
<212> TYPE: DNA
<213> ORGANISM: Artificial Sequence
<220> FEATURE:
<223> OTHER INFORMATION: synthetic

<400> SEQUENCE: 1
tacactttat caaatcttac aatc                                          24

<210> SEQ ID NO 2
<211> LENGTH: 45
<212> TYPE: DNA
<213> ORGANISM: Artificial Sequence
<220> FEATURE:
<223> OTHER INFORMATION: synthetic

<400> SEQUENCE: 2
ttttctagac ggcaggtcag gtacacttta tcaaatctta caatc                   45

<210> SEQ ID NO 3
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: 6-amino-3-(2'-deoxy)-D-ribofuranosyl)-5-nitro-
      1H-pyridin-2-one
```

```
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 3
ttttctagac ggcaggtcag gtananttta tnaaatntta naatn            45

<210> SEQ ID NO 4
<211> LENGTH: 45
<212> TYPE: DNA
<213> ORGANISM: Artificial Sequence
<220> FEATURE:
<223> OTHER INFORMATION: synthetic

<400> SEQUENCE: 4
gattgtaaga tttgataaag tgtacctgac ctgccgtcta gaaaa            45

<210> SEQ ID NO 5
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: 6-amino-3-(2'-deoxy)-D-ribofuranosyl)-5-nitro-
      1H-pyridin-2-one

<400> SEQUENCE: 5
ttttctagac ggcaggtcag gtananttta tnaaatntta naatc            45

<210> SEQ ID NO 6
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
```

```
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (20)..(20)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (22)..(22)
<223> OTHER INFORMATION: 7-amino-9-(1'-beta-D-2'-deoxyribofuranosyl)-
      imidazo[1,2-c]pyrimidin-5(1H)-one

<400> SEQUENCE: 6 gattntaaana tttnataaan tntacctgac ctgccgtcta gaaaa              45

<210> SEQ ID NO 7
<211> LENGTH: 24
<212> TYPE: DNA
<213> ORGANISM: Artificial Sequence
<220> FEATURE:
<223> OTHER INFORMATION: synthetic

<400> SEQUENCE: 7
atcatacata catacaaatc taca                                      24

<210> SEQ ID NO 8
<211> LENGTH: 43
<212> TYPE: DNA
<213> ORGANISM: Artificial Sequence
<220> FEATURE:
<223> OTHER INFORMATION: synthetic

<400> SEQUENCE: 8
gttctcatcc ggggctgtca tcatacatac atacaaatct aca                 43

<210> SEQ ID NO 9
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(22)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
```

```
<220> FEATURE:
<221> NAME/KEY: misc_feature
<222> LOCATION: (42)..(42)
<223> OTHER INFORMATION: 6-amino-3-(2'-deoxy)-D-ribofuranosyl)-5-nitro-
      1H-pyridin-2-one

<400> SEQUENCE: 9
gttctcatcc ggggctgtca tnatanatan atanaaatnt ana                    43

<210> SEQ ID NO 10
<211> LENGTH: 43
<212> TYPE: DNA
<213> ORGANISM: Artificial Sequence
<220> FEATURE:
<223> OTHER INFORMATION: synthetic

<400> SEQUENCE: 10
tgtagatttg tatgtatgta tgatgacagc cccggatgag aac                    43

<210> SEQ ID NO 11
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(22)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 11
gttctcatcc ggggctgtca tnatanatan atanaaatnt aca                    43

<210> SEQ ID NO 12
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (10)..(10)
<223> OTHER INFORMATION: 7-amino-9-(1'-beta-D-2'-deoxyribofuranosyl)-
      imidazo[1,2-c]pyrimidin-5(1H)-one
```

```
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (18)..(18)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (22)..(22)
<223> OTHER INFORMATION: 7-amino-9-(1'-beta-D-2'-deoxyribofuranosyl)-
      imidazo[1,2-c]pyrimidin-5(1H)-one

<400> SEQUENCE: 12 tgtanattttn tatntatnta tnatgacagc cccggatgag aac                    43

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ctactataca tcttactata cttt                                          24

<210> SEQ ID NO 14
<211> LENGTH: 44
<212> TYPE: DNA
<213> ORGANISM: Artificial Sequence
<220> FEATURE:
<223> OTHER INFORMATION: synthetic

<400> SEQUENCE: 14
tcctagacgg caactggggc ctactataca tcttactata cttt                    44

<210> SEQ ID NO 15
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(28)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (31)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (35)..(35)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (40)..(40)
<223> OTHER INFORMATION: 6-amino-3-(2'-deoxy)-D-ribofuranosyl)-5-nitro-
      1H-pyridin-2-one
```

<400> SEQUENCE: 15
tcctagacgg caactggggc tantatanat nttantatan ttt                43

<210> SEQ ID NO 16
<211> LENGTH: 43
<212> TYPE: DNA
<213> ORGANISM: Artificial Sequence
<220> FEATURE:
<223> OTHER INFORMATION: synthetic

<400> SEQUENCE: 16
aaagtatagt aagatgtata gtagccccag ttgccgtcta gga                43

<210> SEQ ID NO 17
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (16)..(16)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (21)..(21)
<223> OTHER INFORMATION: 7-amino-9-(1'-beta-D-2'-deoxyribofuranosyl)-
      imidazo[1,2-c]pyrimidin-5(1H)-one

<400> SEQUENCE: 17
aaantatant aanatntata ntagccccag ttgccgtcta gga                43

<210> SEQ ID NO 18
<211> LENGTH: 24
<212> TYPE: DNA
<213> ORGANISM: Artificial Sequence
<220> FEATURE:
<223> OTHER INFORMATION: synthetic

<400> SEQUENCE: 18
tcaatcaatt acttactcaa atac                                     24

<210> SEQ ID NO 19
<211> LENGTH: 45
<212> TYPE: DNA
<213> ORGANISM: Artificial Sequence
<220> FEATURE:
<223> OTHER INFORMATION: synthetic

<400> SEQUENCE: 19
atgatagagg cataaggagg atcaatcaat tacttactca aatac              45

```
<210> SEQ ID NO 20
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (27)..(27)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 20
atgatagagg cataaggagg atnaatnaat tanttantna aatan                    45

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21
gtatttgagt aagtaattga ttgatcctcc ttatgcctct atcat                    45

<210> SEQ ID NO 22
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (27)..(27)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
      1H-pyridin-2-one
```

```
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 22
atgatagagg cataaggagg atnaatnaat tanttantna aatac                    45

<210> SEQ ID NO 23
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (19)..(19)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (23)..(23)
<223> OTHER INFORMATION: 7-amino-9-(1'-beta-D-2'-deoxyribofuranosyl)-
      imidazo[1,2-c]pyrimidin-5(1H)-one

<400> SEQUENCE: 23
gtatttnant aantaattna ttnatcctcc ttatgcctct atcat                    45
```